(12) United States Patent
Carter

(10) Patent No.: US 9,345,876 B2
(45) Date of Patent: May 24, 2016

(54) COCHLEAR IMPLANT HAVING ELECTRICALLY NONCONDUCTIVE OCCLUDENT FOR TISSUE OPENINGS

(75) Inventor: Paul M. Carter, West Pennant Hills (AU)

(73) Assignee: Cochlear Limited, Macquarie University, NSW (AU)

( * ) Notice: Subject to any disclaimer, the term of this patent is extended or adjusted under 35 U.S.C. 154(b) by 1096 days.

(21) Appl. No.: 13/303,631

(22) Filed: Nov. 23, 2011

(65) Prior Publication Data
US 2012/0071957 A1 Mar. 22, 2012

Related U.S. Application Data

(63) Continuation of application No. 11/614,851, filed on Dec. 21, 2006, now abandoned.

(30) Foreign Application Priority Data

Dec. 21, 2005 (AU) .................................. 2005907188

(51) Int. Cl.
*A61N 1/05* (2006.01)
*A61N 1/00* (2006.01)
*A61F 11/04* (2006.01)
*A61F 2/18* (2006.01)

(52) U.S. Cl.
CPC .................. *A61N 1/0541* (2013.01); *A61F 2/18* (2013.01); *A61F 11/04* (2013.01); *A61N 1/00* (2013.01); *A61N 1/05* (2013.01)

(58) Field of Classification Search
CPC ......... A61N 1/00; A61N 1/05; A61N 1/0541; A61F 2/18; A61F 11/04

USPC .............................. 607/56, 57, 116, 136, 137
See application file for complete search history.

(56) References Cited

U.S. PATENT DOCUMENTS 4,487,210 A 12/1984 Knudsen et al.
4,532,930 A 8/1985 Crosby et al.
(Continued)

FOREIGN PATENT DOCUMENTS

AU 2006252212 7/2007
EP 1972359 9/2008
WO WO 2004/004413 1/2004

OTHER PUBLICATIONS

Austrian Office Action dated Nov. 4, 2010, issued in connection with Austrian Patent Application No. A 576/2009, and partial English-language translation of the Office Action (4 pages).
(Continued)

*Primary Examiner* — Christopher D Koharski
*Assistant Examiner* — Roland Dinga

(57) ABSTRACT

An electrically nonconductive occludent constructed and arranged to forcefully infill a tissue opening so as to effectively prevent transport of electrical current, fluid and bacteria through the tissue opening. A cochlear implant comprising: an elongate electrode carrier member having at least one electrode disposed thereon, wherein the carrier member is configured to traverse a cochleostomy to position the electrodes in the cochlea; and an electrically nonconductive occludent constructed and arranged to circumferentially surround a portion of the carrier member traversing the cochleostomy, and to forcefully infill cochleostomy thereby segregating perilymphatic canals of the cochlea from extracochlear regions.

20 Claims, 6 Drawing Sheets

(56) References Cited

U.S. PATENT DOCUMENTS

| | | | |
|---|---|---|---|
| 4,608,057 | A | 8/1986 | Davis et al. |
| 4,645,504 | A | 2/1987 | Byers |
| 4,795,426 | A * | 1/1989 | Jones .......................... 604/539 |
| 4,892,108 | A | 1/1990 | Miller et al. |
| 4,898,183 | A * | 2/1990 | Kuzma .......................... 607/137 |
| 5,267,968 | A | 12/1993 | Russo |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,628,991 | B2 * | 9/2003 | Kuzma et al. ................ 607/137 |
| 6,697,674 | B2 | 2/2004 | Leysieffer |
| 6,889,094 | B1 | 5/2005 | Kuzma et al. |
| 7,146,227 | B2 | 12/2006 | Dadd et al. |
| 7,194,314 | B1 | 3/2007 | Richter et al. |
| 2002/0156513 | A1 | 10/2002 | Borkan |
| 2004/0225336 | A1 * | 11/2004 | Milojevic et al. ............... 607/57 |
| 2005/0139016 | A1 | 6/2005 | Yamanaka et al. |
| 2005/0256561 | A1 | 11/2005 | Gantz et al. |
| 2007/0135884 | A1 | 6/2007 | Risi |
| 2007/0162098 | A1 | 7/2007 | Risi et al. |
| 2008/0154339 | A1 | 6/2008 | Carter |
| 2008/0234793 | A1 | 9/2008 | Gibson |
| 2009/0254163 | A1 | 10/2009 | Gibson |

OTHER PUBLICATIONS

Cohen, Noel L., "Surgical Techniques for Cochlear Implants," Cochlear Implants, edited by Waltzman et al., 2000, pp. 151-169, Chapter 8, Thieme New York (21 pages).

Gibson et al., "Electrode Design Considerations for Reducing Trauma," $9^{th}$ International Conference on Cochlear Implants and Related Sciences, Jun. 14-17, 2006, Vienna, Austria (16 pages).

Gibson et al., Abstract for "Electrode Design Considerations for Reducing Trauma," $9^{th}$ International Conference on Cochlear Implants and Related Sciences, Jun. 15, 2006, Vienna, Austria (1 page).

Digisonic Convex Receiver document, believed to have been available as of late 2003 (1 page).

Lenarz et al., "Temporal Bone Results and Hearing Conservation with a New Straight Electrode," First International Electro-Acoustic Workshop, Dec. 8-10, 2005, Toulouse (53 pages).

Lenarz et al., "Hearing Conservation Surgery Using the Hybrid-L Electrode," Audiology and Neurotology, Apr. 2009, vol. 14, Supp. 1, pp. 22-31 (10 pages).

European Patent Office, Communication with a Partial European Search Report, issued in connection with European Patent Application No. 08005372.1, dated Dec. 12, 2008 (8 pages).

Lenarz et al., Abstract for Presentation of "Preservation of Residual Hearing with a New Straight Electrode," Jun. 14-17, 2006, Wiener Medizinische Wochenschrift, Abstracts, 2006, pp. 126-127 (4 pages).

Xu et al., "Temporal Bone Surgical Dissection for Cochlear Implantation," for Nucleus Freedom and Nucleus 24 Implants, sent to printers in late 2005 ( 65 pages).

Balkany et al., "Fixation of the Electrode Cable During Cochlear Implantation: the Split Bridge Technique," Laryngoscope 105: Feb. 1995, pp. 217-218.

Extended European Search Report for European Patent Application No. 08 00 5372, dated Dec. 12, 2008.

Cohen et al., "Titanium Clip for Cochlear Implant Electrode Fixation," Clark et al., International Cochlear Implant, Speech and Hearing Symposium, Melbourne 1994; Annals of Otology, Rhinology & Laryngologyk vol. 104, No. 9, Part 2, Supplement 166, Sep. 1995, pp. 402-403.

Lenarz et al., "Temporal Bone Results and Hearing Preservation with a New Straight Electrode," presented at Cochlear Implantation, $1^{st}$ International Electro-Acoustic Workshop, Toulouse, Dec. 8-10, 2005, published at Audiol Neurotol 2006; 11 (suppl 1): pp. 34-41, Oct. 6, 2006.

Lenarz, T., "Introduction of Surgical Concept," $1^{st}$ Hybrid-L Workshop, Hannover, Department of Otolaryngology, Medical University of Hannover, Jun. 13, 2006.

* cited by examiner

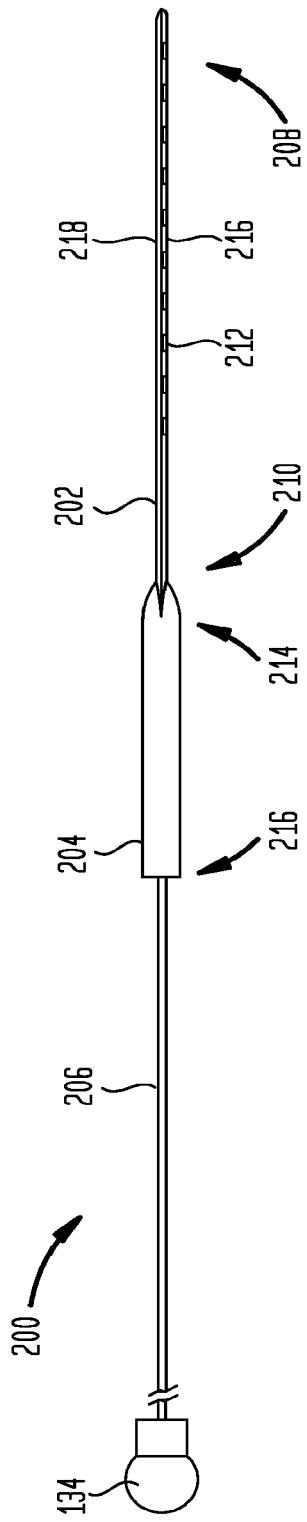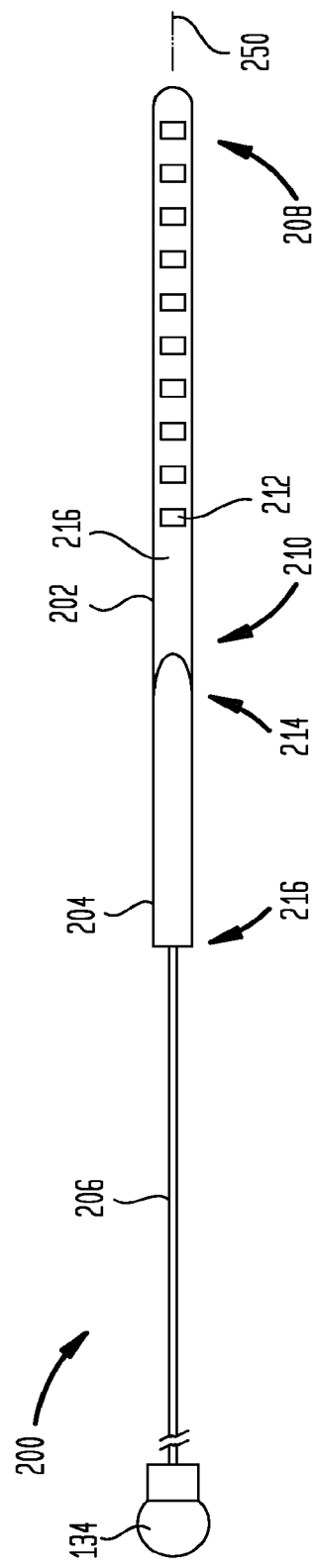

COCHLEAR IMPLANT HAVING ELECTRICALLY NONCONDUCTIVE OCCLUDENT FOR TISSUE OPENINGS

CROSS-REFERENCE TO RELATED APPLICATIONS

This application is a continuation application of U.S. patent application Ser. No. 11/614,851 entitled "COCHLEAR IMPLANT HAVING ELECTRICALLY NONCONDUCTIVE OCCLUDENT FOR TISSUE OPENINGS" and filed on Dec. 21, 2006, which claims priority from Australian Provisional Patent Application No. 2005907188, entitled, "Improved Cochleostomy Sealing" which was filed on Dec. 21, 2005, the contents of each of these applications being incorporated herein by reference in their entirety.

BACKGROUND

1. Field of the Invention

The present invention relates generally to cochlear implant devices, and more particularly, to an electrically nonconductive cochleostomy occludent.

2. Related Art

Hearing loss is generally of two types, namely conductive and sensorineural. The treatment of both of types of hearing loss has been quite different, relying on different principles to deliver sound signals to be perceived by the brain as sound. Conductive hearing loss occurs when the normal mechanical pathways for sound to reach the hair cells in the cochlea are impeded, for example, by damage to the ossicles. In such cases, hearing loss is often improved with the use of conventional hearing aids, which amplify the sound so that acoustic information reaches the cochlear hair cells. Such hearing aids utilize acoustic mechanical stimulation, whereby the sound is amplified according to a number of varying techniques, and delivered to the inner ear as mechanical energy. This may be through a column of air to the eardrum, or through direct delivery to the ossicles of the middle ear.

On the other hand, sensorineural hearing loss is due to the absence or destruction of the cochlear hair cells which are needed to transduce acoustic signals into auditory nerve impulses. Individuals suffering from this type of hearing loss are unable to derive any benefit from conventional hearing aid systems regardless of the volume of the acoustic stimulus. This is because the natural mechanisms for transducing sound energy into auditory nerve impulses are either absent or damaged. In such cases, Cochlear™ implants (also referred to as Cochlear™ devices, Cochlear™ prostheses, Cochlear™ implant systems, and the like; simply "cochlear implants" herein) have been developed to provide the sensation of hearing to such individuals. In cochlear implants, electrical stimulation is provided via stimulating electrodes positioned as close as possible to the nerve endings of the auditory nerve, essentially bypassing the hair cells in a normally functioning cochlea. The application of a stimulation pattern to the nerve endings causes impulses to be sent to the brain via the auditory nerve, resulting in the brain perceiving the impulses as sound.

The electrode array is inserted during an operation that usually takes between 2-3 hours depending on the device to be implanted. An incision is made behind the ear to expose the temporal bone; the temporal bone consists of the squamous, the mastoid, the tympanic, zygomatic and petrous segment. Typically, cochlear implants require the opening of the mastoid bone which leads to the middle ear. A shallow recess is then created to hold the implant package in place substantially level with the bone. Next a hole is drilled which allows the surgeon access into the cochlea. This hole is known as a cochleostomy—the opening from the middle ear to the perilymphatic canals of the cochlea. A cochleostomy may be formed through the round window 141, the oval window 110, the promontory or through the apical turn of the cochlea. The electrode array is then gently threaded into the shell-like structure of the cochlea and the incision closed; the cochleostomy remains open and heals with scar tissue over the next few days.

More recently various alternative approaches have been proposed to cause dynamic volume displacements of the perilymph, some of which require the implantation of an actuator that breaches the cochlea. These procedures require a cochleostomy or equivalent incision to provide the requisite access to the perilymphatic canals of the cochlea.

It is conventional during surgical implantation to use a tissue graft from the patient to provide a seal at the cochleostomy, primarily to reduce the risk of meningitis resulting from communication between the inner ear and the middle ear.

SUMMARY

In one aspect of the invention, an electrically nonconductive occludent is disclosed, the occludent constructed and arranged to forcefully infill a tissue opening so as to effectively prevent transport of electrical current, fluid and bacteria through the tissue opening.

In another aspect of the invention, a cochlear implant is disclosed, the cochlear implant comprising: an elongate electrode carrier member having at least one electrode disposed thereon, wherein the carrier member is configured to traverse a cochleostomy to position the electrodes in the cochlea; and an electrically nonconductive occludent constructed and arranged to circumferentially surround a portion of the carrier member traversing the cochleostomy, and to forcefully infill cochleostomy thereby segregating perilymphatic canals of the cochlea from extracochlear regions.

In a further embodiment of the present invention, a method for implanting an elongate carrier member in a cochlea of a recipient is disclosed, the method comprising: creating a cochleostomy; implanting the carrier member into the cochlea; and positioning an electrically nonconductive occludent in the cochleostomy so as to cause the portion of the carrier member and the occludent to forcefully infill the cochleostomy.

BRIEF DESCRIPTION OF THE DRAWINGS

An illustrative embodiment of the present invention will be described with reference to the accompanying figures, in which:

FIG. 2A is a side view of an electrode assembly in accordance with one embodiment of the present invention;

FIG. 2B is a top view of the electrode assembly illustrated in FIG. 2A;

DETAILED DESCRIPTION

Figure 1:
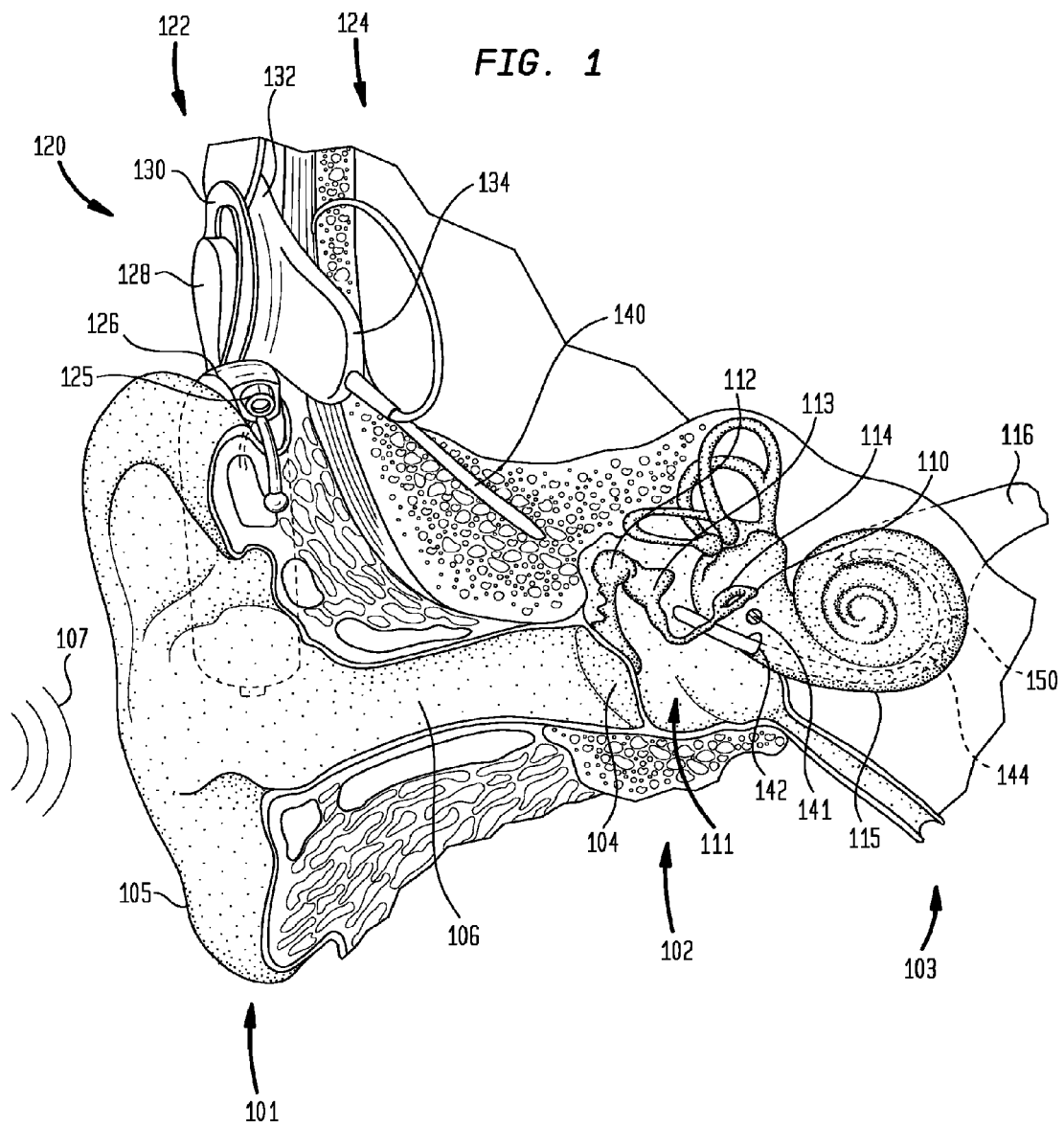
FIG. 1 is a perspective view of an example of an implanted cochlear implant suitable for implementing embodiments of the present invention.

The present invention is generally directed to an electrically nonconductive occludent that forcefully infills and seals a cochleostomy or other tissue opening with or without an implantable component traversing the tissue opening. In one application described herein, an embodiment of the electrically nonconductive occludent is utilized to seal a cochleostomy having an implanted electrode assembly traversing therethrough, or other tissue opening such as the oval or round window with no such implanted component, thereby segregating the perilymphatic canals of the cochlea from extracochlear regions such as the middle ear. In certain embodiments, the occludent has a toroidal cross-sectional shape, circumferentially surrounding the implanted component such as an electrode carrier member.

The occludent may have a combination of one or more characteristics such as shape and durometer to partially enter the cochleostomy and to consume substantially all space between the carrier member and cochlea at the cochleostomy. The occludent may be permanently positioned on the carrier member, or it may be configured to slide over the carrier member to be positioned at the occluding position. In alternative embodiments, the occludent is configured to travel through the carrier member lumen to the occluding position. Such embodiments of the occludent may be configured to travel over the stylet used to implant the carrier member, or may be configured to be inserted with a tool for subsequent expansion. For example, the occludent may be a mechanical structure that is inflated mechanically or with a balloon.

Regardless of the method used to deploy the occludent, the region of the radially distensible carrier member containing the wedge dilates to consume the entire cochleostomy. Advantageously, the present invention provides a high electrical impedance blockage within the cochleostomy, thereby reducing the electric charge which may travel from the electrodes to, for example, an extracochlear reference electrode of the cochlear implant. It should be appreciated that the present invention is operable regardless of the relative size and location of the cochleostomy and carrier member regardless of whether the cochleostomy is formed through round window 141, the oval window 110, the promontory, the apical turn of the cochlea, or at any other therapeutically beneficial location to operatively reduce current flow through a tissue opening and thereby improve the electrical efficiency of the implant.

As noted, openings other than a cochleostomy may be made to accommodate the requirements of other types of prosthetic hearing implants. There are also circumstances that it is desirable to seal round window 141 and/or oval window 110 due to natural conditions, prior surgical procedure, etc. Such openings in tissue, whether they form naturally or occur due to disease, injury or surgery, are collectively and generally referred to herein as a tissue opening.

The present invention may be implemented in a variety of ways and the embodiments illustrated are to be considered only as illustrative constructions. More particularly, the present invention is potentially useful for purposes other than sealing a cochleostomy created as described herein. For example, the present invention may be applied to seal an existing orifice between the middle ear and the inner ear such as round window 141. The present invention may be used to seal any opening created between the middle ear and the perilymph, whether this is intended to be used as a conduit for a part of an implanted device, or to be sealed completely after surgery. The term cochleostomy should accordingly be understood for the purposes of this application in this expansive sense. Such sealing may have further advantages, for example reducing the chance of the recipient contracting meningitis. It may also reduce the risk of unintended explantation.

For the purpose of power reduction it is desirable to reduce the amount of electrical current required to stimulate the auditory nerve. During stimulation, as much as possible the current flowing from the electrode within the cochlea must be directed towards the auditory nerve. Any leakage of current through paths other through than the auditory nerve should therefore be minimised in order to reduce the power consumption of the implant. The present invention accordingly allows current leakage via the cochleostomy of a hearing implant prosthesis to be reduced. As a consequence, the current levels used for stimulation can be decreased as the implant's energy is used more efficiently.

Although many different stimulation approaches have been proposed and used, in each scheme the energy for the stimulations is provided by the implant, and conventionally this is supplied ultimately by the batteries in the external component. Hence, the degree to which the energy supplied by the batteries is effectively delivered impacts upon battery life.

Embodiments of the present invention are described below in connection with one type of stimulating medical device having an component implantable through a tissue opening; that is, a prosthetic hearing implant and, more specifically, a cochlear implant. Cochlear implants use direct electrical stimulation of auditory nerve cells to bypass absent or defective hair cells that normally transduce acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, the cochlear implant provides stimulation of the cochlear nucleus in the brainstem. Such devices, therefore, are commonly referred to as auditory brainstem implants (ABIs).

Exemplary embodiments of a cochlear implant include a Contour™, Freedom™ Nucleus™ or Cochlear™ implant sold by Cochlear Limited, Australia. Such devices are described in U.S. Pat. Nos. 4,532,930, 6,537,200, 6,565,503, 6,575,894, and 6,697,674, the entire contents and disclosures of which are hereby incorporated by reference herein. It should be understood to those of ordinary skill in the art that embodiments of the present invention may be used in other stimulating medical devices such as neurostimulators, cardiac pacemakers/defibrillators, etc. as well as other medical devices which utilize an elongate carrier member to temporarily or permanently implant, deliver or otherwise introduce a therapeutic agent, sensor, device, etc. into a recipient.

FIG. 1 is a cut-away view of the relevant components of outer ear 101, middle ear 102 and inner ear 103, which are described next below. In a fully functional ear, outer ear 101 comprises an auricle 105 and an ear canal 106. An acoustic pressure or sound wave 107 is collected by auricle 105 and channeled into and through ear canal 106. Disposed across the distal end of ear cannel 106 is a tympanic membrane 104 which vibrates in response to acoustic wave 107. This vibration is coupled to oval window, or fenestra ovalis, 110 through three bones of middle ear 102, collectively referred to as the ossicles 111.

Ossicles 111 comprises the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells (not shown) to auditory nerve 116 and, ultimately, to the brain where they are perceived as sound. In some persons experiencing sensorineural hearing loss, there is an absence or destruction of the hair cells. Cochlear implant 120 is utilized to directly stimulate the ganglion cells to provide a hearing sensation to such persons.

FIG. 1 also shows how cochlear implant 120 is positioned in relation to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is provided to a behind-the-ear (BTE) speech processing unit 126 that generates coded signals. The coded signals are provided to an external transmitter unit 128, along with power from a power source (not shown) such as a battery. External transmitter unit 128 comprises an external coil 130 and, preferably, a magnet (not shown) secured directly or indirectly in external coil 130.

Internal component assembly 124 comprises an internal receiver unit 132 having an internal coil (not shown) that transcutaneously receives power and coded signals from external assembly 122, and provides such signals to a stimulator unit 134. In response to the coded signals, stimulator 134 applies stimulation signals to cochlea 115 via an implanted electrode assembly 140. Electrode assembly 140 enters cochlea 115 via a cochleostomy 142, and has an array 144 of one or more electrodes 150 positioned to be substantially aligned with portions of tonotopically-mapped cochlea 115. The delivery of stimulation signals at various locations along cochlea 115 causes a hearing percept representative of the received sound 107.

While cochlear implant 120 is described as having external components, in another embodiment, the controller, including the microphone, speech processor and power supply, may also be implantable. In such embodiments, the controller may be contained within a hermetically sealed housing or the housing used for stimulator unit 134.

Electrode assembly 140 preferably assumes an optimal electrode position in cochlea 115 upon or immediately following implantation into the cochlea. It is also desirable that electrode assembly 140 be configured such that the insertion process causes minimal trauma to the sensitive structures of cochlea 115. Usually electrode assembly 140 is pre-curved, held in a straight configuration at least during the initial stages of the implantation procedure, conforming to the natural shape of the cochlea during and subsequent to implantation.

FIG. 2A is a side view of an embodiment of electrode assembly 140, referred to herein as electrode assembly 200. FIG. 2B is a top view of electrode assembly 200. Electrode assembly 200 comprises a carrier member 202, a stop member 204 and lead 206. Carrier member 202 has a distal end 208 adapted to be implanted furthest into cochlea 115, and a proximal end 210 connected to a distal end 214 of laterally-extending stop member 204. The opposing proximal end 216 of stop member 204 is connected to lead 206. Lead 206 physically and electrically connects electrode assembly 200 with stimulator unit 134.

When implanted in a recipient, the surface of carrier member 202 which faces the interior of cochlea 115 is referred to herein as the medial surface 216 of carrier member 202. The opposing side of carrier member 202, referred to herein as lateral surface 218, faces the external wall and bony capsule (not shown) of cochlea 115. It should be understood that the terms medial surface, medial direction, and the like, are generally used herein to refer to the surfaces, features and directions toward the center of cochlea 115, while the terms lateral surface, lateral direction, and the like, are generally used herein to refer to surfaces, features and directions toward the exterior of cochlea 115. In addition, a longitudinal axis 250 is utilized herein to facilitate descriptions herein.

A plurality of spaced-apart electrodes 212 are mounted on or in carrier member 202. Electrodes 212 may be disposed in a linear or non-linear array on or in carrier member 202, and may be positioned to align with predetermined regions of tonotopically mapped cochlea 115. In alternative embodiments, electrodes 212 are implemented as described in U.S. Provisional Patent Applications 60/748,217, 60/748,273 and 60/748,314, hereby incorporated by reference herein.

Figure 3:
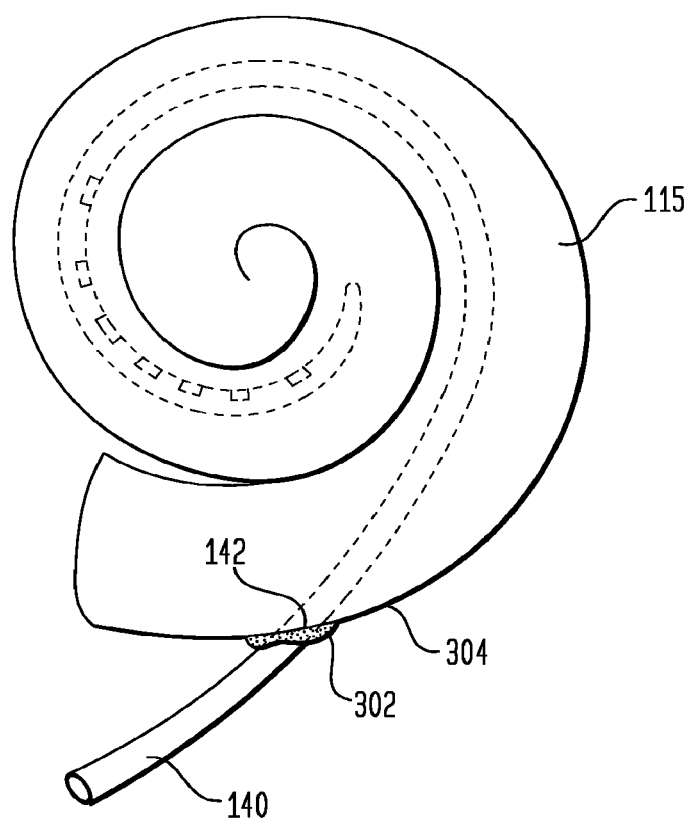
FIG. 3 is a schematic diagram of the cochlea showing a conventional intra-cochlear electrode insertion with the cochleostomy sealed using muscle/fat tissue.

FIG. 3 is a schematic of cochlear 115 showing a conventional, intra-cochlear electrode insertion, where cochleostomy 142 is sealed using a graft 302 of the recipient's tissue, typically muscle and fat. In this illustrative example, cochleostomy 142 is shown in an exterior wall 304 of cochlea 115, and is situated in the space of middle ear 102. Graft 302 is positioned around carrier member 140 over cochleostomy 142, as shown in FIG. 3.

Figure 4:
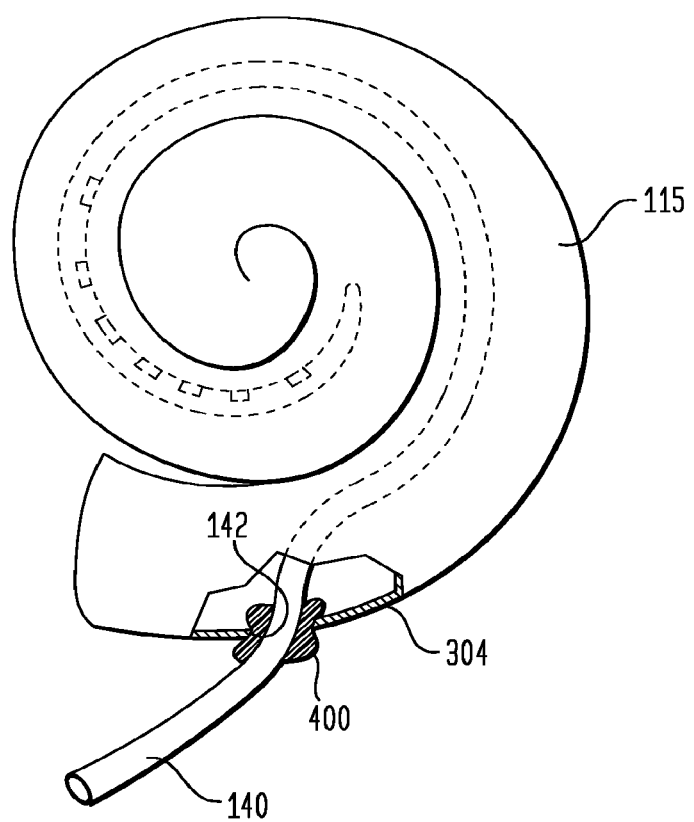
FIG. 4 is a cross-sectional view of a portion of a cochlea showing an improved cochleostomy seal in accordance with one embodiment of the present invention.

FIG. 4 is a cross-sectional view of a portion of a cochlea showing an improved cochleostomy seal in accordance with one embodiment of the present invention. In this exemplary embodiment, a deformable electrically nonconductive occludent 400 is inserted into cochleostomy 142 to prevent the transfer of fluids, bacteria and electrical current through cochleostomy 142. In one particular embodiment, occludent 400 is formed from a soft, deformable grade of silicone elastomer. Such combination of characteristics allows occludent 400 to elastically conform to the generally irregular shape of cochleostomy 142.

Occludent 400 may be formed around elongate electrode carrier member 140 so that it can slide along the carrier member. For example, in one embodiment, occludent 400 has an aperture suitable for slidingly receiving the implantable component that is to be traversing through the tissue opening, here carrier member 140 traversing cochleostomy 142. In practice, the surgeon would insert electrode carrier member 140 through cochleostomy 142 and into cochlea 115 in a conventional manner. This process is well understood in the art, and described in the literature, and conventional aspects of this process will not be further described in detail. A standard reference for such a process is described in "Surgical Techniques for Cochlear Implants", Noel L. Cohen, Chapter 8, p 151 in "Cochlear Implants", Waltzman, S. B. and Cohen, L. L. (1997) ISBN 0-86577-882-5, the disclosure of which is hereby incorporated by reference.

The extent of insertion will vary significantly from recipient to recipient, depending upon the peculiarities of the anatomy of the recipient, the specific surgical procedure used by the surgeon, and the precise location of cochleostomy 142. It is expected that the most improvement in leakage reduction will be for the basal electrodes 150, as these electrodes have the shortest leakage path. It therefore also follows that greater improvement may be seen in short or partial electrode arrays, for example as used in electro-acoustic stimulation.

After carrier member 140 has been inserted as far as desired, occludent 400 may be slid along electrode carrier member 140 to be partially inside cochlea 115 and partially outside cochlea 115; that ins occludent 400 infills cochleostomy 142. Because this embodiment of occludent 400 has an exterior radius that is larger than the interior radius of cochleostomy 142, and because occludent 400 is malleable; that is, has a low durometer, it deforms to partially enter cochlea 115 thereby forcefully infilling cochleostomy 142 so as to effectively prevent transport of electrical current, fluid and bacteria through the cochleostomy. In other words, occludent 400 fills the available space between the walls of cochlea 115 defining cochleostomy 142 and the exterior of carrier member 140 which passes through the cochleostomy. Furthermore, occludent 400 sufficiently infills cochleostomy 142 so that fluids, bacteria, etc., cannot pass through an remaining apertures between cochlea 115 and occludent 400. Thus, occludent 400 provides a seal of electrically nonconductive, or insulating, biocompatible material within cochleostomy 142. Occludent 400 thereby increases the impedance of the undesired current path through cochleostomy 142 to the reference electrode (not shown) of cochlear implant 120 located outside the inner ear 103. It should be appreciated to those of ordinary skill in the art that as the anatomical structures surrounding occludent 400 are partially conductive and, as such, electric current may still leak through this general region, but current leakage through cochleostomy 142 will be reduced.

Figure 5:
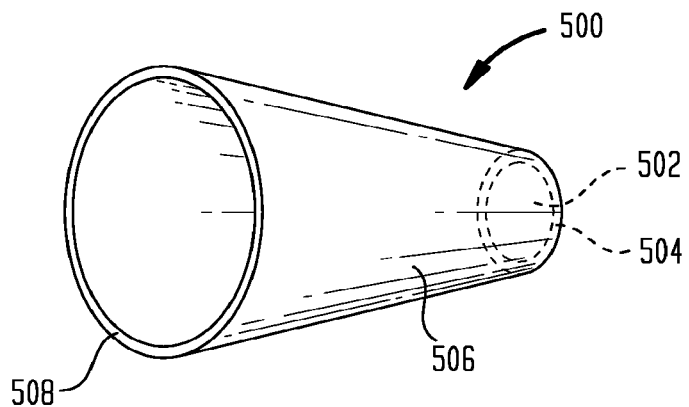
FIG. 5 is a perspective view of one embodiment of the electrically nonconductive occludent of the present invention.
Figure 6:
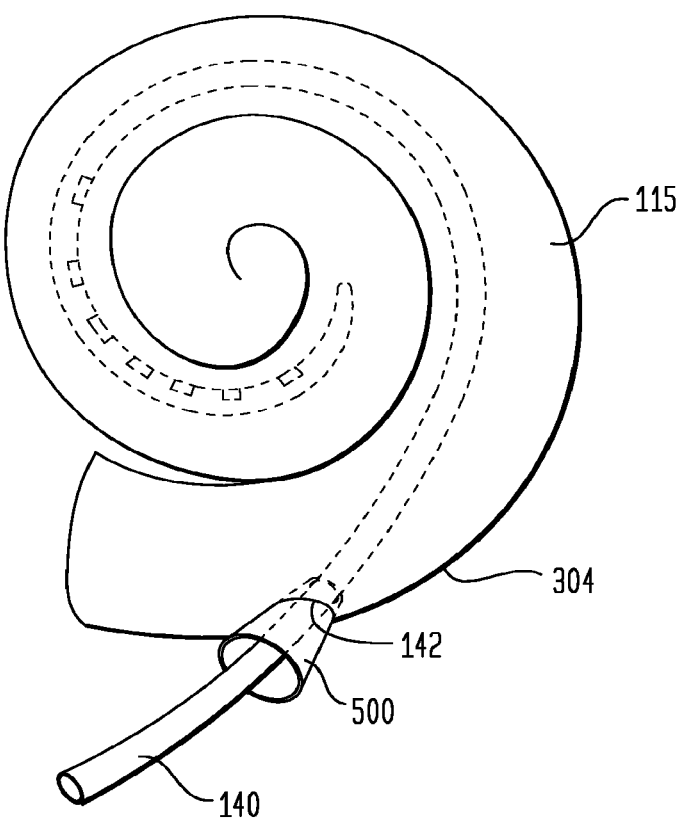
FIG. 6 is a perspective view of a human cochlea showing the embodiment of the occludent illustrated in FIG. 5 implanted in a cochleostomy, in accordance with embodiments of the present invention.

The embodiment of occludent 400 shown in FIG. 4 is generally toroidal in shape, as it surrounds electrode carrier member 140 and infills cochleostomy 142 as described above. However, any other suitable shape may be used. One such suitable shape is a truncated cone 500, as shown in FIGS. 5 and 6. FIG. 5 is a perspective view of an occludent 500 having a truncated cone configuration, while FIG. 6 is a perspective view of occludent 500 inserted into cochleostomy 142 of cochlea 115.

The end 504 of truncated cone occludent 500 which is has a smaller diameter is dimensioned to easily pass through cochleostomy 142 to enable occludent 500 to enter cochlea 115. Conversely, the end 508 of occludent 500 which is has a relatively greater diameter is dimensioned to no pass through cochleostomy 142. As such, occludent 500 forcefully infills cochleostomy 142 as it is inserted into the cochleostomy, thereby sealing cochlea 115. In one embodiment, body 506 of occludent 500 is also malleable to enable the occludent to deform in response to the forced insertion of the occludent, further insuring a forceful infilling sufficient to seal cochleostomy 142. As shown in FIG. 6, when implanted, base 508 of occludent 500 remains on the outside of cochleostomy 142, allowing for easy removal should that be necessary.

As noted above with reference to the embodiment of the electrically nonconducting occludent 400, occludent 500 may be implemented as an integrated or unitary element of electrode carrier member 140, or it may be a separately manufactured component that has a channel 502 dimensioned to slide over carrier member 140. In either embodiment, once electrode carrier member 140 is in a suitable position and occludent 500 is in the occluding position; that is, partially infilling cochleostomy 142, occludent 400 seals cochleostomy 142.

Occludent 500 may be formed of any suitable inert biocompatible material that is operatively an electrical insulator. In one embodiment, occludent 500 is preferably formed of silicone. It should be appreciated, however, that occludent 500 may be formed of different materials or from a combination of one or more other material. It could be partly formed from a more stiff material, with the outer portions being resilient in order to provide the necessary conformable seal.

Occludent 500 may be formed from a suitable polymer putty material in situ. It could be formed, with a slit or the like, to allow it to be attached around the electrode carrier member 140 after insertion. Importantly, occludent 500 is formed of an insulating material and substantially seal cochleostomy 142 so as increase the impedance of the leakage path. If different shapes or forms of electrode carrier member 140 are used, then the shape of the occludent 500 will need to be adapted to suit the shape of the implanted carrier member which traverses cochleostomy 142.

Figure 7:
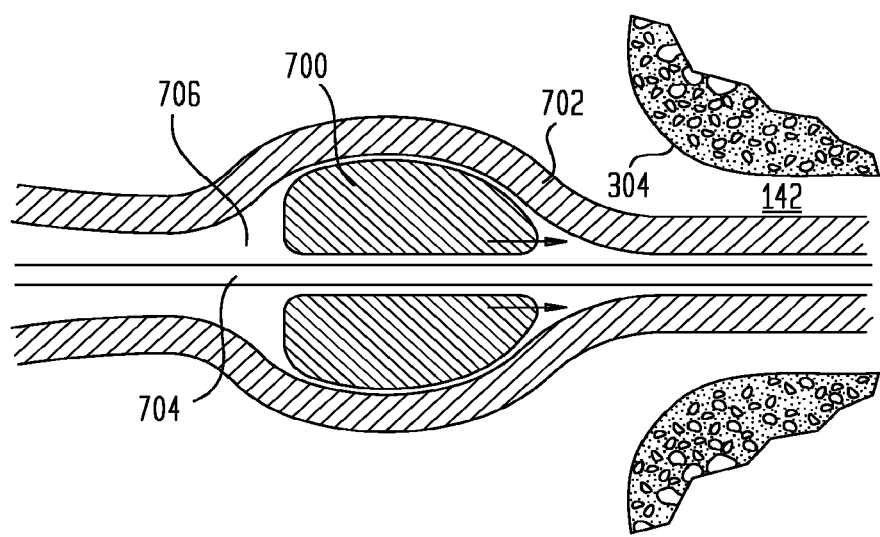
FIG. 7 is a cross-sectional view of an alternative embodiment of a cochleostomy occludent of the present invention.

Alternatively, as shown in FIG. 7, an alternative embodiment of the present invention, carrier member 140 is radially distensible and has a longitudinally-extending lumen 706. In one embodiment, lumen 706 is configured to receive a stylet as is conventionally utilized in certain pre-curved electrode carrier members. In an alternative embodiment, lumen 706 is configured to interoperate with occludent 700 as described herein.

Occludent 700 is configured to be slidingly passed through lumen 706 as shown in FIG. 7. The exterior dimensions of occludent 700 are larger than the interior dimensions of lumen 706. As such, occludent 700 applied a force radially outward in that region of carrier member 702 in which occludent 700 is located. Because carrier member 702 is outwardly distensible, such force causes carrier member 702 to dilate or expand in the region containing occludent 700, as shown in FIG. 7. In such embodiments, advancing occludent 700 to be partially inside cochlea 115; that is, to infill cochleostomy 142, causes carrier member 702 to expand to abut the perimeter of cochlea 115 that defines cochleostomy 142.

Occludent 700 may take on any form necessary. In the embodiment shown in FIG. 7, occludent 700 is solid. Alternatively occludent 700 may be hollow. In the embodiment shown in FIG. 7, occludent 700 is distally tapered and has round edges. This is to avoid damage to in interior surfaces of carrier member 702 defining lumen 706. it should be appreciated, however, that occludent 700 may take on other shapes in alternative embodiments.

In operation, occludent 700 is initially located near a proximal end of electrode carrier member 702 so that it does not interfere with the normal insertion of the carrier member. After insertion of electrode carrier member 702, occludent 700 is slid along lumen 706 to cochleostomy 142 where it deforms the sides of carrier member 702 sufficiently to seal the cochleostomy 142. This embodiment has the further advantage in that two separate components do not abut to create a potential space, thereby reducing the risk of infection.

It should be appreciated that tools or guide wires may be used to facilitate the advancement of occludent 700 in lumen 706. For example, in the example shown in FIG. 7, a guide wire 704 is provided, and occludent 700 has an aperture for sliding receiving the guide wire 704. Alternatively, occludent 700 may be detachably secured to the distal end of a tool that may be advance into lumen 706.

Alternatively, occludent 700 may be formed by being moulded as part of the electrode moulding process, at an appropriate location along the length of electrode carrier member 702. In such embodiments, implantation of electrode carrier member 702 is performed until occludent 700 is positioned in cochleostomy 142.

Such an embodiment has the same advantage as the sliding space filling plug of FIG. 7 in that it has no separate insulator parts abutting and therefore has a reduced risk of infection. It also has the advantage of not requiring a small device to be moved, relative to the array, in the confined space and delicate structures of the inner ear during implantation.

In alternative embodiment, occludent 700 may be initially of smaller dimensions when advanced through lumen 706, and then expanded to a larger size to effect the radial distension of carrier member 702 noted above. Such an expansion may be achieved in many ways now or later developed, such as by implementing mechanically expandable members, a material that expands in response to the pumping of air or other fluid, the mixing of materials, and the like.

It should also be appreciated that the occludent of the present invention may be specifically shaped to fit an actual aperture, for example the oval window. Alternatively, it could be formed in situ, for example by a fast curing sealant injected around the cochleostomy 142. Any effective artificial seal which can be positioned as required may be used to implement the invention.

The efficacy of implementing embodiments of the present invention has been investigated using an animal model. Experiments on two Guinea Pigs, with a total of three ears investigated acutely have been performed. In these experiments, the bulla (middle ear cavity) was exposed, a cochleostomy was drilled over the round window and a four electrode array was inserted. Stimulation was applied between the most apical intracochlear electrode (ICE) and a monopolar ball electrode inserted in the temporalis muscle.

Monopolar Electrical Auditory Brainstem Response (EABR) thresholds and the voltage waveform between the stimulus electrodes (to deduce impedance) were measured. In the last of the three ears investigated the voltage between the two most basal ring electrodes was also measured during the stimulus pulse (to determine the current flow along the cochlea at a point near the cochleostomy).

To calibrate this measurement a known current pulse had been previously applied between the most apical ICE and another ring electrode (on a separate array) held by hand in the cochleostomy.

Four different methods of sealing the cochleostomy were used: no sealing; small piece of muscle of approx. the volume of the cochleostomy; larger piece of muscle several times the volume of the cochleostomy (residual muscle extending out of the cochleostomy) and otoform paste (one ear only).

Otoform paste is a settable silicone material, used in hearing aid fitting and similar applications, which is initially mouldable but which then sets to a soft deformable consistency.

In every ear the EABR thresholds, the impedance and the current flow at the cochleostomy varied depending on the plug type used. The following table shows the four sealing methods and how those parameters varied:

| Plug material | EABR T | Impedance (Z) | Cochleostomy current |
| --- | --- | --- | --- |
| Large muscle | Largest | lowest | Largest |
| Small muscle | $2^{nd}$ largest | $2^{nd}$ lowest | $2^{nd}$ largest |
| No seal | $3^{rd}$ largest | $3^{rd}$ lowest | $3^{rd}$ largest |
| Otoform putty | Smallest | highest | smallest |

The smallest EABR threshold (otoform putty) was about 40% smaller than the largest threshold (large muscle). The impedance results varied by around 20-35% from smallest to largest. The current flow through the cochleostomy varied from 84% of total current (large muscle) to 70% (otoform putty).

The results are consistent with a significant proportion of the stimulus current flowing through the cochleostomy. Different sealing arrangements appear to change the amount of current flow through the cochleostomy and thereby change the EABR threshold. The changes in impedance and cochleostomy current flow as measured by the voltage on the basal two rings are consistent with this model. These results indicate it is possible to lower thresholds by effective sealing of the cochleostomy.

Another perspective is that any T and C decrease gained from using the plug will manifest itself as a decrease in power consumption of the implant and a subsequent increase in battery life. Power consumption of the implant can be divided into two parts—power consumed to run the implant electronics ($W_E$) and power consumed to deliver current to the auditory nerve ($W_N$). The decrease in T/C level current will manifest itself as a proportional decrease in $W_N$. For present implant designs the ratio of $W_N$ to $W_E$ is about 50:50 for high rate strategies. If, for example, it is assumed that the plug provides a 10% decrease in T/C level this would translate to about a 5% decrease in overall implant power consumption for high rate strategies, less for lower rate strategies. However, the most recent tests show that the plug yields an improvement of between 20-40% decrease in T/C level, indicating at lease a 10% improvement in power consumption.

Variations and additions are possible to the structures described within the general scope of the present invention. For example, embodiments of the present invention may be employed in addition to a tissue graft type sealing approach.

Although the present invention has been principally described with reference to a cochlear implant prosthesis, it will be appreciated that embodiments of the present invention may readily be applied to provide a nonconductive seal of a tissue opening regardless of whether a carrier member 140 or other implant prosthesis or component is positioned within the tissue opening. Such applications in which there are electrical losses through the tissue opening may particularly benefit from the present invention. It should also be understood that although the description has referred principally to a prosthetic hearing implant with an external receiver/stimulator unit 134, embodiments of the present invention are equally applicable to a totally implanted device.

It will also be appreciated that although this invention has been principally used to provide sealing at the cochleostomy there are other tissue openings between cochlea 115 and middle ear 102 that may pass similar electric current and that may also provide similar benefit by being sealed with an embodiment of the electrically nonconductive occludent of the present invention. These include round window 141 and oval window 110. Embodiments of the electrically nonconductive occludent of the present invention which are not integrated in or unitary with a carrier member may be inserted into these other tissue openings, providing a further decrease in stray electrical current. It will be understood that the present invention may also be applied to seal a cochleostomy which is not intended to remain open, for example in some form of totally implanted device which does not require a physical conduit to remain out of inner ear 103.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An electrode array of a cochlear implant, comprising:
an elongate electrode carrier member having at least one electrode disposed thereon, wherein the carrier member is configured to traverse an opening in a cochlea to position the at least one electrode in the cochlea, wherein
at least a first portion of the carrier member is configured to be circumferentially distensible and circumferentially dilatable to infill a gap between the carrier member and the opening and thereby segregate intra-cochlear regions from extracochlear regions,
wherein the first portion of carrier member includes a channel extending there through, and wherein the carrier member is configured such that pressure applied to a channel wall of the channel circumferentially distends the carrier member to infill the gap between the carrier member and the opening.

2. The electrode array of claim 1, wherein:
the first portion of the carrier member configured to be dilatable such that the electrode array abuts the opening.

3. The electrode array of claim 1, wherein:
the carrier member has an outer surface extending about the first portion; and
the first portion of the carrier member is configured to be circumferentially dilatable such that the outer surface abuts the opening to forcefully infill the gap between the carrier member and the opening and thereby segregate intra-cochlear regions from extracochlear regions.

4. The electrode array of claim 3, wherein:
the outer surface extends without discontinuity from a location proximate the first portion to a location distal of the first portion.

5. The electrode array of claim 3, wherein:
the outer surface extends without discontinuity from a location outside the cochlea to a location inside the cochlea when infilling the gap.

6. The electrode array of claim 5, wherein:
the first portion is configured to be circumferentially dilatable such that a first portion of the outer surface is distended to have diameters greater than a second portion of the outer surface;
the second portion of the outer surface corresponds to an undistensed portion of the outer surface; and
the second portion extends in the longitudinal direction towards a distal end of the carrier member at least about half a longitudinal distance of extension of the first portion.

7. The electrode array of claim 1, further comprising:
a body configured to move in a longitudinal direction within the carrier member to circumferentially distend the carrier member to infill the gap between the carrier member and the opening.

8. The electrode array of claim 7, wherein:
the body is an occludent; and
the occludent is configured to be advanced within the carrier member to a location at least partially within the cochlea to infill the gap between the carrier member and the opening.

9. The electrode array of claim 1, further comprising:
an occludent configured to slide along the channel and expand the lumen wall outward from a first diameter less than an outer diameter of the occludent to a second diameter at least about equal to the outer diameter of the occludent to infill the gap between the carrier member and the opening.

10. The electrode array of claim 1, wherein:
the elongate electrode carrier is configured to be variably circumferentially distensible in a longitudinal direction of the carrier member.

11. A method of implanting an elongate carrier member of a cochlear implant in a cochlea of a recipient, comprising:
implanting the carrier member into an intra-cochlear region of the cochlea through a passageway from an extracochlear region into the cochlea, wherein the elongate electrode carrier member includes at least one electrode disposed thereon, and at least a first portion of the carrier member is configured to be variably circumferentially distensible in a longitudinal direction of the carrier member; and
circumferentially dilating a portion the carrier member to infill the passageway and thereby segregate the intra-cochlear region from the extracochlear region.

12. The method of claim 11, further comprising:
positioning an occludent at least partially into the passageway so as to expand the portion of the carrier member thereby circumferentially dilating the portion of the carrier member to infill the passageway.

13. The method of claim 11, wherein:
the action of implanting the carrier member into the cochlea is performed before circumferentially dilating the portion of the carrier member to infill the passageway.

14. The method of claim 13, wherein:
the action of circumferentially dilating the portion of the carrier member to infill the passageway is performed by sliding a body inside the carrier member in the distal direction of the carrier member such that at least a portion of the body is located within the passageway.

15. An electrode array of a cochlear implant, comprising:
an elongate electrode carrier member having at least one electrode disposed thereon, wherein the carrier member is configured to traverse an opening in a cochlea to position the at least one electrode in the cochlea, wherein
the carrier member is configured to permit fluid flow from intracochlear regions to extracochlear regions and visa-versa at a first time after insertion of the electrode array at a first position, and the carrier member is configured to infill a gap between the carrier member and the opening present after insertion of the electrode array to a desired position to segregate intracochlear regions from extracochlear regions to prevent fluid flow from intracochlear regions to extracochlear regions and visa-versa at a second time after insertion of the electrode array at the first position without moving a component to a location between an outer surface of the carrier member and the opening in the cochlea, without moving at least an outer portion of the carrier member relative to the opening, and without moving the electrode array from the desired position, wherein the second time period is after the first time period.

16. The electrode array of claim 15, wherein:
the carrier member is configured to maintain the gap at a first time after insertion of the electrode array at a first position; and
the carrier member is configured to infill the gap a second time after insertion of the electrode array at the first position without moving a component to a location between an outer surface of the carrier member and the opening in the cochlea, wherein the second time period is after the first time period.

17. The electrode array of claim 15, wherein:
the carrier member is configured to infill a gap between the carrier member and the opening without a non-integral component to the carrier member positioned between the carrier member and the opening.

18. The electrode array of claim 15, wherein at least a first portion of the carrier member is configured to be variably circumferentially distensible to infill a gap between the carrier member and the opening and thereby segregate intracochlear regions from extracochlear regions.

19. The electrode array of claim 18, further comprising:
a body configured to move in a longitudinal direction within the carrier member to circumferentially distend the carrier member to infill the gap between the carrier member and the opening.

20. The electrode array of claim 18, wherein the carrier member includes a channel extending through the first portion of carrier member, wherein the carrier member is configured such that pressure applied to a channel wall of the channel circumferentially distends the carrier member to infill the gap between the carrier member and the opening.

* * * * *